(12) United States Patent
Stroefer et al.

(10) Patent No.: US 7,999,140 B2
(45) Date of Patent: Aug. 16, 2011

(54) METHOD FOR THE PRODUCTION OF POLYOXYMETHYLENE DIALKYL ETHERS FROM TRIOXAN AND DIALKYLETHERS

(75) Inventors: Eckhard Stroefer, Mannheim (DE); Heiner Schelling, Kirchheim (DE); Hans Hasse, Kaiserslautern (DE); Sergej Blagov, Stuttgart (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 152 days.

(21) Appl. No.: 11/917,192

(22) PCT Filed: Jun. 12, 2006

(86) PCT No.: PCT/EP2006/063074
§ 371 (c)(1),
(2), (4) Date: Dec. 12, 2007

(87) PCT Pub. No.: WO2006/134081
PCT Pub. Date: Dec. 21, 2006

(65) Prior Publication Data
US 2008/0207955 A1   Aug. 28, 2008

(30) Foreign Application Priority Data
Jun. 15, 2005   (DE) .......................... 10 2005 027 690

(51) Int. Cl.
*C07C 41/18*   (2006.01)
(52) U.S. Cl. ...................................... 568/613
(58) Field of Classification Search ........................ None
See application file for complete search history.

(56) References Cited

U.S. PATENT DOCUMENTS

| 2,449,469 A | | 9/1948 | William et al. |
| 2,471,134 A | | 5/1949 | Wright |
| 2,512,950 A | * | 6/1950 | Londergan .................... 528/242 |
| 5,746,785 A | | 5/1998 | Moulton et al. |
| 6,166,266 A | * | 12/2000 | Hagen et al. .................. 568/613 |
| 6,392,102 B1 | | 5/2002 | Hagen et al. |
| 2007/0260094 A1 | * | 11/2007 | Schelling et al. ............. 568/600 |

FOREIGN PATENT DOCUMENTS

| EP | 1070755 | | 1/2001 |
| GB | 603872 | * | 6/1948 |
| WO | WO 2006/045506 A1 | * | 5/2006 |

OTHER PUBLICATIONS

U.S. Appl. No. 12/466,460, filed Apr. 21, 2009, Boehling, et al.

* cited by examiner

*Primary Examiner* — Rosalynd Keys
(74) *Attorney, Agent, or Firm* — Oblon, Spivak, McClelland, Maier & Neustadt, L.L.P.

(57) ABSTRACT

A process for preparing polyoxymethylene dialkyl ethers of the formula $$H_{2m+1}C_mO(CH_2O)_nC_mH_{2m+1}$$

where n=2-10,
  m, identically or differently,=1 or 2,
in which a dialkyl ether selected from dimethyl ether, methyl ethyl ether and diethyl ether, and trioxane are fed into a reactor and reacted in the presence of an acidic catalyst, the amount of water introduced into the reaction mixture by the dialkyl ether, trioxane and/or the catalyst being <1% by weight based on the reaction mixture.

19 Claims, 3 Drawing Sheets

METHOD FOR THE PRODUCTION OF POLYOXYMETHYLENE DIALKYL ETHERS FROM TRIOXAN AND DIALKYLETHERS

The invention relates to a process for preparing polyoxymethylene dialkyl ethers.

Polyoxymethylene dimethyl ethers constitute a homologous series of the general formula $$CH_3O(CH_2O)_nCH_3$$

in which n is $\geq 1$. Like the parent molecule of the homologous series, methylal $CH_3O(CH_2O)CH_3$ (n=1), the polyoxymethylene dimethyl ethers are acetals. They are prepared by reacting methanol with aqueous formaldehyde in the presence of an acidic catalyst. Like other acetals, they are stable under neutral or alkaline conditions, but are attacked even by dilute acids. Hydrolysis converts them in a first step to hemiacetals and methanol. In a second step, the hemiacetals are hydrolyzed to formaldehyde and methanol.

On the laboratory scale, polyoxymethylene dimethyl ethers are prepared by heating polyoxymethylene glycol or paraformaldehyde with methanol in the presence of traces of sulfuric acid or hydrochloric acid at temperatures of from 150 to 180° C. and reaction times of from 12 to 15 hours. This results in decomposition reactions to form carbon dioxide and to the formation of dimethyl ether. At a paraformaldehyde or polyoxymethylene glycol:methanol ratio of 6:1, polymers where n>100, generally n=300-500, are obtained. The products are washed with sodium sulfite solution and subsequently fractionated by fractional crystallization.

U.S. Pat. No. 2,449,469 describes a process in which methylal is heated with paraformaldehyde or a concentrated formaldehyde solution in the presence of sulfuric acid. This affords polyoxymethylene dimethyl ethers with from 2 to 4 formaldehyde units per molecule.

In recent times, polyoxymethylene dimethyl ethers have gained significance as diesel fuel additives. To reduce smoke and soot formation in the combustion of conventional diesel fuel, oxygen compounds which contain only few, if any, C—C bonds, for example methanol, are added to it. However, such compounds are frequently insoluble in diesel fuel and lower the cetane number and/or the flashpoint of the diesel fuel mixture.

U.S. Pat. No. 5,746,785 describes the preparation of polyoxymethylene dimethyl ethers having a molar mass of from 80 to 350, corresponding to n=1-10, by reaction of 1 part of methylal with 5 parts of paraformaldehyde in the presence of 0.1% by weight of formic acid at a temperature of from 150 to 240° C., or by reaction of 1 part of methanol with 3 parts of paraformaldehyde at a temperature of from 150 to 240° C. The resulting polyoxymethylene dimethyl ethers are added to a diesel fuel in amounts of from 5 to 30% by weight.

U.S. Pat. No. 6,392,102 describes the preparation of polyoxymethylene dimethyl ethers by reacting a starting stream comprising methanol and formaldehyde, which has been obtained by oxidation of dimethyl ether, in the presence of an acidic catalyst and simultaneous separation of the reaction products in a catalytic distillation column. This affords methylal, methanol, water and polyoxymethylene dimethyl ethers.

EP-A 1 070 755 discloses the preparation of polyoxymethylene dimethyl ethers with from 2 to 6 formaldehyde units in the molecule by reaction of methylal with paraformaldehyde in the presence of trifluorosulfonic acid. This forms polyoxymethylene dimethyl ethers where n=2-5 with a selectivity of 94.8%, the dimer (n=2) being obtained to an extent of 49.6%. The resulting polyoxymethylene dimethyl ethers are added to a diesel fuel in amounts of from 4 to 11% by weight.

A disadvantage of the known processes for preparing the lower polyoxymethylene dimethyl ethers (where n=1-10) is that the dimer is obtained to a quite predominant extent. A disadvantage of the processes which start from formaldehyde and methanol is additionally that water is formed as a reaction product and hydrolyzes already formed polyoxymethylene dimethyl ethers in the presence of the acidic catalysts. This forms unstable hemiacetals. The unstable hemiacetals lower the flashpoint of the diesel fuel mixture and thus impair its quality. However, too low a flashpoint of the diesel fuel mixture leads to the specifications laid down by relevant DIN standards no longer being fulfilled. Owing to comparable boiling points, hemiacetals are difficult to remove from polyoxymethylene dimethyl ethers. The dimer formed as the main product has a low boiling point and thus likewise reduces the flashpoint, as a result of which it is less suitable as a diesel fuel additive.

It is an object of the invention to provide an improved process for preparing polyoxymethylene dialkyl ethers which does not have the disadvantages of the prior art. It is a particular object of the invention to provide a process for preparing polyoxymethylene dialkyl ethers which are particularly suitable as diesel fuel additives. Particularly suitable are the polyoxymethylene dimethyl ethers and polyoxymethylene diethyl ethers where n=3 and 4 (trimer, tetramer). It is a particular object of the invention to provide a process for preparing polyoxymethylene dialkyl ethers with a particularly high proportion of trimer.

The object is achieved by a process for preparing polyoxymethylene dialkyl ethers of the formula $$H_{2m+1}C_mO(CH_2O)_nC_mH_{2m+1}$$

where n=2-10, m, identically or differently,=1 or 2, in which a dialkyl ether selected from dimethyl ether (DME), methyl ethyl ether and diethyl ether (DEE), and trioxane are fed into a reactor and reacted in the presence of an acidic catalyst, the amount of water introduced into the reaction mixture by the dialkyl ether, trioxane and/or the catalyst being <1% by weight based on the reaction mixture.

It is also possible to use mixtures of the dialkyl ethers. Preference is given to carrying out the reaction with DME.

The use of dialkyl ether as the reactant allows the reaction to be carried out substantially anhydrously, since water is not formed as a by-product, as can be taken from the following reaction equation:

$$CH_3OCH_3+(CH_2O)_3 \rightarrow CH_3O—(CH_2O)_3—CH_3$$

In the presence of water or alcohols, chemical reactions which would lead to a multitude of poly(oxymethylene) glycols and hemiformals would proceed. Reactive azeotropes would be formed and would lead to complex phase behavior in the attempted distillative separation.

The reaction of dialkyl ether and trioxane is carried out generally at a temperature of from −20 to +200° C., preferably from 0 to 150° C., and a pressure of from 1 to 200 bar, preferably from 2 to 100 bar. The molar dialkyl ether:trioxane ratio is generally from 0.1 to 10, preferably from 0.5 to 5.

In principle, paraformaldehyde can also be used instead of trioxane. However, the use of paraformaldehyde has the disadvantage that the selectivity for the desired oligomers falls. This makes the recycle streams in the process very large. Moreover, paraformaldehyde comprises terminal OH groups and thus leads to the release of water in the reaction.

The acidic catalyst may be a homogeneous or heterogeneous acidic catalyst. Suitable acidic catalysts are mineral acids such as substantially anhydrous sulfuric acid, sulfonic acids such as trifluoromethanesulfonic acid and para-toluenesulfonic acid, heteropolyacids, acidic ion exchange resins, zeolites, aluminosilicates, silicon dioxide, aluminum oxide, titanium dioxide and zirconium dioxide. In order to increase their acid strength, oxidic catalysts may be doped with sulfate or phosphate groups, generally in amounts of from 0.05 to 10% by weight. The reaction may be carried out in a stirred tank reactor (CSTR) or a tubular reactor. When a heterogeneous catalyst is used, preference is given to a fixed bed reactor. When a fixed catalyst bed is used, the product mixture may subsequently be contacted with an anion exchange resin in order to obtain a substantially acid-free product mixture.

The total amount of water introduced by dialkyl ether and trioxane and by the catalyst is <1% by weight, preferably <0.5% by weight, more preferably <0.2% by weight and in particular <0.1% by weight, based on the reaction mixture composed of dialkyl ether, trioxane and the catalyst. To this end, virtually anhydrous trioxane and dialkyl ether are used, and the amount of water correspondingly introduced, if appropriate, by the catalyst is restricted. The hemiacetals (monoethers) and polyoxymethylene glycols formed by hydrolysis in the presence of water from already formed polyoxymethylene dialkyl ether have a comparable boiling point to the polyoxymethylene dialkyl ethers, which complicates removal of the polyoxymethylene dialkyl ethers from these by-products.

In order to selectively obtain polyoxymethylene dialkyl ethers where n=3 and n=4 (trimer, tetramer), a fraction comprising the trimer and tetramer is removed from the product mixture of the reaction of dialkyl ether with trioxane, and unconverted dialkyl ether, trioxane and polyoxymethylene dialkyl ether where n<3 are recycled into the acid-catalyzed reaction. In a further embodiment of the process according to the invention, the polyoxymethylene dialkyl ethers where n>4 are additionally also recycled into the reaction. As a result of the recycling, a particularly large amount of trimer is obtained.

In a particularly preferred embodiment, a first fraction comprising dialkyl ether, preferably DME, a second fraction comprising the dimer (n=2) and trioxane, a third fraction comprising the trimer and tetramer (n=3, 4) and a fourth fraction comprising the pentamer and higher homologs (n>4) are obtained from the product mixture of the acid-catalyzed reaction of dialkyl ether, preferably DME, with trioxane. In this context, it is especially preferred to carry out the separation of the product mixture of the acid-catalyzed reaction of dialkyl ether with trioxane in three distillation columns connected in series, the first fraction being removed from the product mixture of the reaction in one distillation column or an evaporator, the second fraction being removed from the remaining mixture in a second distillation column, and the remaining mixture being separated into the third and the fourth fraction in a third distillation column. In this separation, the first distillation column or the evaporator may be operated, for example, at a pressure of from 0.1 to 100 bar, the second distillation column, for example, at a pressure of from 0.05 to 1 bar and the third distillation column, for example, at a pressure of from 0.001 to 0.5 bar. Preference is given to recycling the first and the second fraction, more preferably additionally also the fourth fraction, into the reaction.

When a homogeneous catalyst, for example a mineral acid or a sulfonic acid is used, it remains in the fourth fraction and is recycled with it into the acid-catalyzed reaction.

Figure 1:
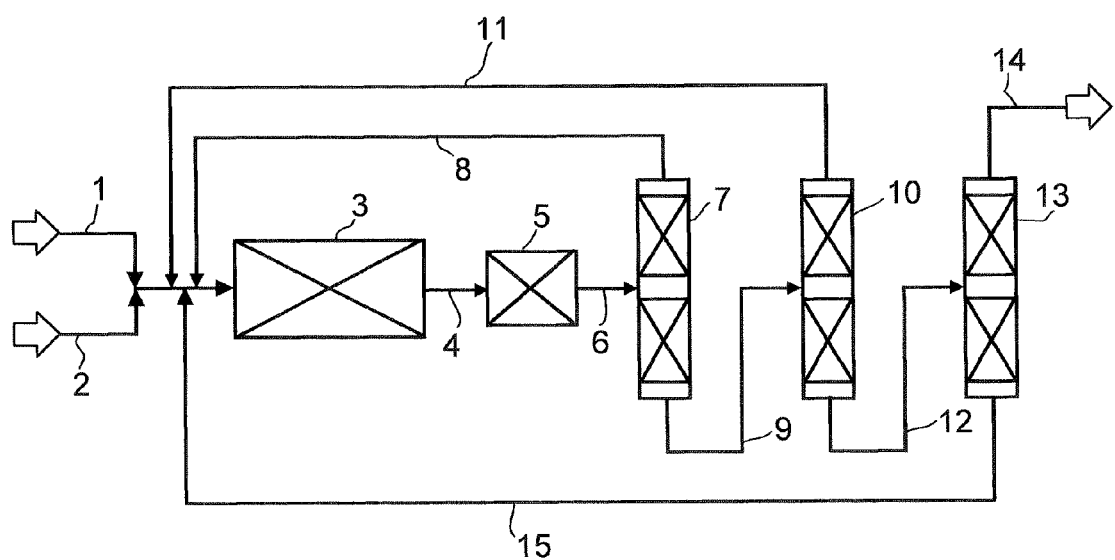
FIG. 1 reproduces a process flow diagram according to one embodiment of the process according to the invention.
Figure 2:
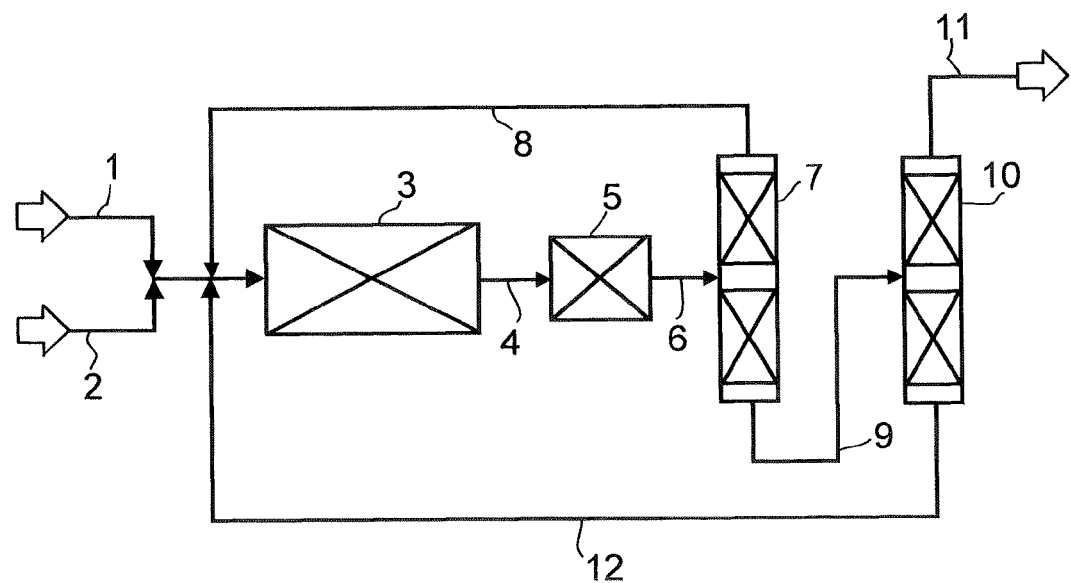
FIG. 2 reproduces the process flow diagram according to a further embodiment of the process according to the invention. In contrast to the process shown in FIG. 1, the first and the second distillation column are combined here to a single distillation column 7. This may also be a divided column, as described, for example, in U.S. Pat. No. 2,471,134. Accordingly, a recycle stream 8 composed of dialkyl ether, dimer (n=2) and trioxane, and a recycle stream 12 composed of pentameric polyoxymethylene dialkyl ether and higher polyoxymethylene dialkyl ethers (n>4) are obtained. The bottom draw stream 9 of the distillation column 7 is fed to a second column 10 in which the mixture of trimeric and tetrameric polyoxy-methylene dialkyl ether (n=3, 4) is removed overhead.
Figure 3:
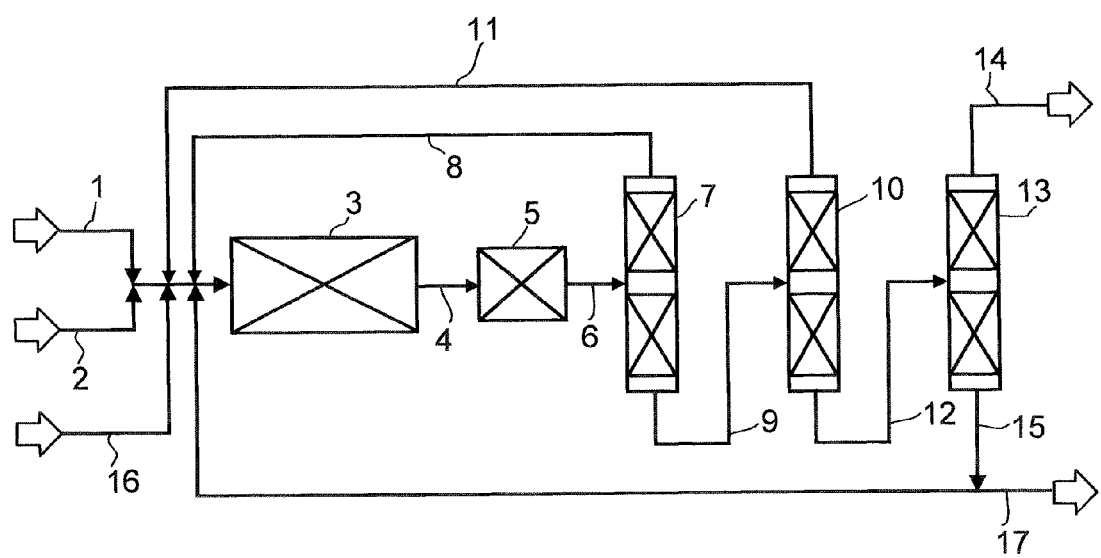
FIG. 3 reproduces the process flow diagram of a further embodiment of the process according to the invention. In contrast to the process according to FIG. 1, a homogeneous catalyst is used and is fed into the reactor 3 as a further feed stream 16. A bed composed of anionic ion exchange resin downstream of the reactor 3 can also be dispensed with and the product stream 4 of the reaction fed directly to the first distillation column 7. The bottom draw 15 of the third distillation column additionally comprises the homogeneous catalyst. A small substream 17 can be removed from the recycle stream 15 and discharged from the process, in which case the catalyst loss can be compensated by the starting stream 16.

The invention is illustrated in detail below with reference to the drawing.

A starting stream 1 composed of dialkyl ether and a starting stream 2 composed of trioxane are fed together with the recycle streams 8, 11 and 15 into the reactor 3 and reacted there in the presence of a heterogeneous acidic catalyst to give the product mixture 4 which comprises dialkyl ether, trioxane and polyoxymethylene dialkyl ether where n=from 2 to 10. The product stream 4 is passed through a bed 5 composed of anion exchange resin to obtain a substantially acid-free product mixture 6. This is fed into a first distillation column 7 in which dialkyl ether is removed overhead as a recycle stream 8. The bottom draw 9 of the first column 7 is introduced into a second distillation column 10 in which the dimer (n=2) and trioxane are removed overhead as recycle stream 11. The bottom draw stream 12 of the second distillation column 10 is fed to a third column 13 in which a mixture of trimeric and tetrameric polyoxymethylene dialkyl ether (n=3, 4) is removed overhead. At the column bottom, a recycle stream 15 composed of pentameric and higher polyoxymethylene dialkyl ethers (n>4) is obtained.

EXAMPLES

Example 1

30 g of trioxane and 63 g of dimethyl ether are heated with 0.2 g of sulfuric acid at 100° C. for 16 hours. After 1, 2, 3, 4, 5, 6, 7, 8 and 16 hours, a sample is taken and analyzed by gas chromatography in each case. After 8 hours, the equilibrium composition has been attained. DME escapes upon decompression. The composition was characterized as follows: 18% n=2, 58% n=3, 16% n=4, remainder n>4 and sampling/analysis errors.

Example 2

17 g of trioxane, 20 g of DME and 15 g of Amberlite® IR 120 ion exchange resin are heated at 100° C. for 24 hours.

After 24 hours, a sample is taken and analyzed by gas chromatography. The mixture comprises polyoxymethylene dimethyl ethers in the following distribution (in % by weight): 19% n=2, 64% n=3, 1% n=4, remainder n>4.

What is claimed is:

1. A process for preparing a polyoxymethylene dialkyl ether of the following formula:

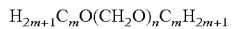

wherein n is an integer of from 2 to 10, and each m is independently 1 or 2, and wherein said process comprises:

reacting a reaction mixture comprising:
- a dialkyl ether selected from the group consisting of dimethyl ether, methyl ethyl ether and diethyl ether;
- trioxane; and
- an acidic catalyst,
- wherein said reaction mixture comprises less than 1 wt. % of water, based on a total weight of said reaction mixture, and
- wherein said reaction mixture does not contain methanol;

obtaining by distillation from said reaction mixture a fraction comprising polyoxymethylene dialkyl ether where n='and 4; and recycling dialkyl ether, trioxane and polyoxymethylene dialkyl ether where n<3 and optionally n>4 into the reaction mixture.

2. The process according to claim 1, wherein a first fraction comprising dialkyl ether, a second fraction comprising polyoxymethylene dialkyl ether where n=2 and trioxane, a third fraction comprising polyoxymethylene dialkyl ether where n=3 and 4, and a fourth fraction comprising polyoxymethylene dialkyl ether where n>4 are obtained from the reaction mixture.

3. The process according to claim 2, wherein the first fraction is removed from the reaction mixture in a first distillation column, the second fraction is removed from the remaining mixture in a second distillation column and the remaining mixture is separated into the third and the fourth fraction in a third distillation column.

4. The process according to claim 2, wherein the first and the second fraction are recycled into the reaction mixture.

5. The process according to claim 4, wherein the fourth fraction is recycled into the reaction mixture.

6. The process according to claim 3, wherein the first distillation column is operated at a pressure of from 0.1 to 100 bar, the second distillation column at a pressure of from 0.05 to 1 bar and the third distillation column at a pressure of from 0.001 to 0.5 bar.

7. The process according to claim 1, wherein said reaction mixture comprises less than 0.5 wt. % of water, based on a total weight of said reaction mixture.

8. The process according to claim 1, wherein the acidic catalyst is a homogeneous or heterogeneous catalyst selected from the group consisting of mineral acids, sulfonic acids, heteropolyacids, acidic ion exchange resins, zeolites, aluminosilicates, silicon dioxide, aluminum oxide, titanium dioxide and zirconium dioxide.

9. The process according to claim 1, wherein the reaction is carried out at a pressure of from 1 bar to 200 bar and a temperature of from −20° C. to +200° C.

10. The process according to claim 1, wherein the dialkyl ether is dimethyl ether.

11. The process according to claim 1, wherein said reaction mixture comprises less than 0.2 wt. % of water, based on a total weight of said reaction mixture.

12. The process according to claim 1, wherein said reaction mixture comprises less than 0.1 wt. % of water, based on a total weight of said reaction mixture.

13. The process according to claim 1, wherein said reaction mixture does not contain water.

14. The process according to claim 1, wherein said reaction mixture does not contain alcohol.

15. The process according to claim 1, wherein said reaction mixture does not contain formaldehyde.

16. The process according to claim 1, wherein said reaction mixture does not contain paraformaldehyde.

17. The process according to claim 1, wherein said reaction mixture does not contain water, methanol, formaldehyde and paraformaldehyde.

18. The process according to claim 1, wherein said reaction mixture consists essentially of said dialkyl ether, said trioxane and said acidic catalyst.

19. The process according to claim 1, wherein said reaction mixture consists of said dialkyl ether, said trioxane and said acidic catalyst.

* * * * *